(12) United States Patent
Surti

(10) Patent No.: US 9,345,476 B2
(45) Date of Patent: May 24, 2016

(54) TACKING DEVICE AND METHODS OF DEPLOYMENT

(75) Inventor: Vihar C. Surti, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 246 days.

(21) Appl. No.: 12/787,744

(22) Filed: May 26, 2010

(65) Prior Publication Data

US 2010/0305591 A1    Dec. 2, 2010

Related U.S. Application Data

(60) Provisional application No. 61/181,946, filed on May 28, 2009.

(51) Int. Cl.
*A61B 17/064* (2006.01)
*A61B 17/00* (2006.01)

(52) U.S. Cl.
CPC ..... *A61B 17/064* (2013.01); *A61B 2017/00862* (2013.01); *A61B 2017/00867* (2013.01); *A61B 2017/0649* (2013.01)

(58) Field of Classification Search
CPC ............... A61F 2220/0008; A61F 2220/0016; A61B 17/12122; A61B 17/064; A61B 2017/0649
USPC ......... 606/139, 142, 143, 151, 157, 158, 213, 606/215, 232; 623/23.72–23.76
See application file for complete search history.

(56) References Cited

U.S. PATENT DOCUMENTS

| | | | |
|---|---|---|---|
| 2,199,025 | A | 4/1940 | Conn |
| 2,671,444 | A | 3/1954 | Pease, Jr. |
| 3,209,422 | A | 10/1965 | Dritz |
| 3,399,432 | A | 9/1968 | Merser |
| 3,470,834 | A | 10/1969 | Bone |
| 3,556,079 | A | 1/1971 | Omizo |

(Continued)

FOREIGN PATENT DOCUMENTS

| | | | |
|---|---|---|---|
| EP | 0310582 A1 | 4/1989 | |
| EP | 0774237 A2 | 5/1997 | |

(Continued)

OTHER PUBLICATIONS

Communication Pursuant to Rules 161(1) and 162EPC for European Patent Application Serial No. 09791618.3, dated Mar. 28, 2011, 2 pages.

(Continued)

*Primary Examiner* — Thomas McEvoy
(74) *Attorney, Agent, or Firm* — Brinks Gilson & Lione

(57) ABSTRACT

The present embodiments provide apparatus and methods suitable for coupling a graft member to tissue, closing a bodily opening, and the like. In one embodiment, a tacking device comprises a wire having first and second ends, and further having delivery and deployed states. In the contracted state, the wire comprises an elongated configuration that is substantially parallel to a central longitudinal axis. In the expanded state, the wire comprises a head region and a body region, the head region comprising at least one full turn having a first diameter, and the body region comprising at least two full turns having a second diameter, wherein the first diameter is greater than the second diameter. One or more of the tacking devices may be delivered using a laparoscopic, endoscopic or percutaneous approach.

5 Claims, 4 Drawing Sheets

(56) References Cited

U.S. PATENT DOCUMENTS

| | | | |
|---|---|---|---|
| 3,814,104 A | 6/1974 | Irnich et al. |
| 3,856,016 A | 12/1974 | Davis |
| 3,954,108 A | 5/1976 | Davis |
| 3,958,576 A | 5/1976 | Komiya |
| 4,006,747 A | 2/1977 | Kronenthal et al. |
| 4,204,541 A | 5/1980 | Kapitanov |
| 4,217,902 A | 8/1980 | March |
| 4,235,238 A | 11/1980 | Ogiu et al. |
| 4,485,816 A | 12/1984 | Krumme |
| 4,621,639 A | 11/1986 | Transue et al. |
| 4,749,114 A | 6/1988 | Green |
| 4,773,420 A | 9/1988 | Green |
| 4,791,707 A | 12/1988 | Tucker |
| 4,796,627 A | 1/1989 | Tucker |
| 4,821,939 A | 4/1989 | Green |
| 4,832,027 A | 5/1989 | Utz |
| 4,990,156 A | 2/1991 | Lefebvre |
| 4,994,069 A * | 2/1991 | Ritchart et al. ............... 606/191 |
| 5,015,249 A | 5/1991 | Nakao et al. |
| 5,049,153 A | 9/1991 | Nakao et al. |
| 5,059,205 A | 10/1991 | El-Nounou et al. |
| 5,084,057 A | 1/1992 | Green et al. |
| 5,099,827 A | 3/1992 | Melzer et al. |
| 5,100,420 A | 3/1992 | Green et al. |
| 5,123,914 A | 6/1992 | Cope |
| 5,156,609 A | 10/1992 | Nakao et al. |
| 5,192,303 A | 3/1993 | Gatturna et al. |
| 5,203,787 A | 4/1993 | Noblitt et al. |
| 5,242,456 A | 9/1993 | Nash et al. |
| 5,324,307 A | 6/1994 | Jarrett et al. |
| 5,333,624 A | 8/1994 | Tovey |
| 5,334,217 A | 8/1994 | Das |
| 5,350,385 A | 9/1994 | Christy |
| 5,366,480 A | 11/1994 | Corriveau et al. |
| 5,368,600 A | 11/1994 | Failla et al. |
| 5,368,602 A | 11/1994 | de la Torre |
| 5,411,522 A | 5/1995 | Trott |
| 5,417,691 A | 5/1995 | Hayhurst |
| 5,437,266 A | 8/1995 | McPherson |
| 5,520,700 A | 5/1996 | Beyar et al. |
| 5,527,343 A | 6/1996 | Bonutti |
| 5,554,183 A | 9/1996 | Nazari |
| 5,573,543 A | 11/1996 | Akopov et al. |
| 5,582,615 A | 12/1996 | Foshee et al. |
| 5,582,616 A | 12/1996 | Bolduc et al. |
| 5,593,414 A | 1/1997 | Shipp et al. |
| 5,662,683 A | 9/1997 | Kay |
| 5,667,527 A | 9/1997 | Cook |
| 5,674,231 A | 10/1997 | Green et al. |
| 5,690,656 A | 11/1997 | Cope et al. |
| 5,695,525 A | 12/1997 | Mulhauser et al. |
| 5,728,116 A | 3/1998 | Rosenman |
| 5,741,278 A | 4/1998 | Stevens |
| 5,779,720 A | 7/1998 | Walder-Utz et al. |
| 5,810,848 A | 9/1998 | Hayhurst |
| 5,865,791 A | 2/1999 | Whayne et al. |
| 5,868,763 A | 2/1999 | Spence et al. |
| 5,891,159 A | 4/1999 | Sherman et al. |
| 5,968,078 A | 10/1999 | Grotz |
| 5,972,002 A | 10/1999 | Bark et al. |
| 5,972,022 A | 10/1999 | Huxel |
| 5,976,159 A | 11/1999 | Bolduc et al. |
| 5,984,917 A | 11/1999 | Fleischman et al. |
| 5,984,949 A | 11/1999 | Levin |
| 6,110,183 A | 8/2000 | Cope |
| 6,113,612 A | 9/2000 | Swanson et al. |
| RE36,974 E | 11/2000 | Bonutti |
| 6,149,658 A | 11/2000 | Gardiner et al. |
| 6,152,935 A | 11/2000 | Kammerer et al. |
| 6,152,937 A | 11/2000 | Peterson et al. |
| 6,156,044 A | 12/2000 | Kammerer et al. |
| 6,159,223 A | 12/2000 | Danks et al. |
| 6,171,321 B1 | 1/2001 | Gifford, III et al. |
| 6,183,486 B1 | 2/2001 | Snow et al. |
| 6,193,732 B1 | 2/2001 | Frantzen et al. |
| 6,228,055 B1 | 5/2001 | Foerster et al. |
| 6,241,747 B1 | 6/2001 | Ruff |
| 6,290,674 B1 | 9/2001 | Roue et al. |
| 6,306,150 B1 | 10/2001 | Levinson |
| 6,328,727 B1 | 12/2001 | Frazier et al. |
| 6,371,963 B1 | 4/2002 | Nishtala et al. |
| 6,375,671 B1 * | 4/2002 | Kobayashi et al. ............ 606/213 |
| 6,402,765 B1 | 6/2002 | Monassevitch et al. |
| 6,419,669 B1 | 7/2002 | Frazier et al. |
| 6,425,887 B1 | 7/2002 | McGuckin et al. |
| 6,425,900 B1 | 7/2002 | Knodel et al. |
| 6,428,548 B1 | 8/2002 | Durgin et al. |
| 6,446,854 B1 | 9/2002 | Remiszewski et al. |
| 6,447,530 B1 | 9/2002 | Ostrovsky et al. |
| 6,468,290 B1 | 10/2002 | Weldon et al. |
| 6,482,178 B1 | 11/2002 | Andrews et al. |
| 6,491,707 B2 | 12/2002 | Makower et al. |
| 6,551,333 B2 | 4/2003 | Kuhns et al. |
| 6,572,629 B2 | 6/2003 | Kalloo et al. |
| 6,592,559 B1 | 7/2003 | Pakter et al. |
| 6,623,510 B2 | 9/2003 | Carley et al. |
| 6,641,557 B1 | 11/2003 | Frazier et al. |
| 6,699,256 B1 | 3/2004 | Logan et al. |
| 6,699,263 B2 | 3/2004 | Cope |
| 6,712,804 B2 | 3/2004 | Roue et al. |
| 6,719,777 B2 | 4/2004 | Ginn et al. |
| 6,746,458 B1 | 6/2004 | Cloud |
| 6,746,460 B2 | 6/2004 | Gannoe et al. |
| 6,746,472 B2 | 6/2004 | Frazier et al. |
| 6,776,783 B1 | 8/2004 | Frantzen et al. |
| 6,849,078 B2 | 2/2005 | Durgin et al. |
| 6,884,248 B2 | 4/2005 | Bolduc et al. |
| 6,911,032 B2 | 6/2005 | Jugenheimer et al. |
| 6,913,607 B2 | 7/2005 | Ainsworth et al. |
| 6,966,916 B2 | 11/2005 | Kumar |
| 6,994,713 B2 | 2/2006 | Berg et al. |
| 7,001,398 B2 | 2/2006 | Carley et al. |
| 7,018,388 B2 | 3/2006 | Yencho et al. |
| 7,025,756 B2 | 4/2006 | Frazier et al. |
| 7,056,325 B1 | 6/2006 | Makower et al. |
| 7,060,084 B1 | 6/2006 | Loshakove et al. |
| 7,087,073 B2 | 8/2006 | Bonutti |
| 7,112,214 B2 | 9/2006 | Peterson et al. |
| 7,115,110 B2 | 10/2006 | Frazier et al. |
| 7,211,101 B2 | 5/2007 | Carley et |
| 7,326,221 B2 | 2/2008 | Sakamoto |
| 7,326,231 B2 | 2/2008 | Phillips et al. |
| 7,331,968 B2 | 2/2008 | Arp et al. |
| 7,410,460 B2 | 8/2008 | Benderev |
| 7,416,554 B2 | 8/2008 | Lam et al. |
| 7,485,124 B2 | 2/2009 | Kuhns et al. |
| 7,494,496 B2 | 2/2009 | Swain et al. |
| 7,601,159 B2 | 10/2009 | Ewers et al. |
| 7,608,091 B2 | 10/2009 | Goldfarb et al. |
| 7,618,426 B2 | 11/2009 | Ewers et al. |
| 7,621,925 B2 | 11/2009 | Saadat et al. |
| 7,622,068 B2 | 11/2009 | Li et al. |
| 7,641,836 B2 | 1/2010 | Li et al. |
| 7,655,015 B2 | 2/2010 | Goldfarb et al. |
| 7,666,197 B2 | 2/2010 | Orban, III |
| 7,670,362 B2 | 3/2010 | Zergiebel |
| 7,695,493 B2 | 4/2010 | Saadat et al. |
| 7,704,264 B2 | 4/2010 | Ewers et al. |
| 7,722,628 B2 | 5/2010 | Stokes et al. |
| 7,727,247 B2 | 6/2010 | Kimura et al. |
| 7,727,248 B2 | 6/2010 | Smith et al. |
| 7,736,376 B2 | 6/2010 | Sato et al. |
| 7,736,378 B2 | 6/2010 | Maahs et al. |
| 7,736,379 B2 | 6/2010 | Ewers et al. |
| 7,736,388 B2 | 6/2010 | Goldfarb et al. |
| 7,744,613 B2 | 6/2010 | Ewers et al. |
| 7,758,598 B2 | 7/2010 | Conlon et al. |
| 7,758,612 B2 | 7/2010 | Shipp |
| 7,799,040 B2 | 9/2010 | Stokes et al. |
| 7,803,165 B2 | 9/2010 | Stokes et al. |
| 7,803,166 B2 | 9/2010 | Stokes et al. |
| 7,815,652 B2 | 10/2010 | Messerly et al. |
| 7,815,653 B2 | 10/2010 | Stokes et al. |
| 7,815,659 B2 | 10/2010 | Conlon et al. |

(56) References Cited

U.S. PATENT DOCUMENTS

| | | |
|---|---|---|
| 7,815,662 B2 | 10/2010 | Spivey et al. |
| 7,828,811 B2 | 11/2010 | Kortenbach et al. |
| 7,842,053 B2 * | 11/2010 | Chanduszko et al. ........ 606/157 |
| 2001/0002250 A1 | 5/2001 | Burbank et al. |
| 2001/0037130 A1 | 11/2001 | Adams |
| 2001/0039435 A1 | 11/2001 | Roue et al. |
| 2002/0010481 A1 * | 1/2002 | Jayaraman ................. 606/151 |
| 2002/0099437 A1 * | 7/2002 | Anson et al. ................ 623/1.15 |
| 2003/0158578 A1 | 8/2003 | Pantages et al. |
| 2003/0195561 A1 | 10/2003 | Carley et al. |
| 2004/0009289 A1 | 1/2004 | Carley et al. |
| 2004/0039414 A1 | 2/2004 | Carley et al. |
| 2004/0044364 A1 | 3/2004 | Devries et al. |
| 2004/0073236 A1 | 4/2004 | Carley et al. |
| 2004/0087981 A1 | 5/2004 | Berube et al. |
| 2004/0087985 A1 | 5/2004 | Loshakove et al. |
| 2004/0092975 A1 | 5/2004 | Loshakove et al. |
| 2004/0097982 A1 | 5/2004 | Jugenheimer et al. |
| 2004/0167539 A1 | 8/2004 | Kuehn et al. |
| 2004/0186514 A1 | 9/2004 | Swain et al. |
| 2004/0220596 A1 | 11/2004 | Frazier et al. |
| 2005/0015141 A1 | 1/2005 | Quiachon et al. |
| 2005/0033313 A1 | 2/2005 | Chu et al. |
| 2005/0038370 A1 | 2/2005 | Kuth et al. |
| 2005/0113851 A1 | 5/2005 | Swain et al. |
| 2005/0119695 A1 | 6/2005 | Carley et al. |
| 2005/0143763 A1 | 6/2005 | Ortiz et al. |
| 2005/0171562 A1 | 8/2005 | Criscuolo et al. |
| 2005/0182445 A1 | 8/2005 | Zamierowski |
| 2005/0192596 A1 | 9/2005 | Jugenheimer et al. |
| 2005/0197594 A1 | 9/2005 | Burbank et al. |
| 2005/0234512 A1 | 10/2005 | Nakao |
| 2005/0251154 A1 * | 11/2005 | Chanduszko et al. ........ 606/151 |
| 2005/0251165 A1 | 11/2005 | Vaughan et al. |
| 2005/0273119 A1 * | 12/2005 | Widomski et al. ............. 606/151 |
| 2005/0277945 A1 | 12/2005 | Saadat et al. |
| 2005/0277981 A1 | 12/2005 | Maahs et al. |
| 2005/0283188 A1 | 12/2005 | Loshakove et al. |
| 2006/0004409 A1 | 1/2006 | Nobis et al. |
| 2006/0004410 A1 | 1/2006 | Nobis et al. |
| 2006/0015006 A1 | 1/2006 | Laurence et al. |
| 2006/0015125 A1 | 1/2006 | Swain |
| 2006/0025788 A1 | 2/2006 | Loshakove et al. |
| 2006/0025819 A1 | 2/2006 | Nobis et al. |
| 2006/0106279 A1 | 5/2006 | Machold et al. |
| 2006/0106405 A1 | 5/2006 | Fann et al. |
| 2006/0116605 A1 | 6/2006 | Nakao |
| 2006/0135989 A1 | 6/2006 | Carley et al. |
| 2006/0155288 A1 | 7/2006 | Little et al. |
| 2006/0167484 A1 | 7/2006 | Carley et al. |
| 2006/0190016 A1 | 8/2006 | Onuki et al. |
| 2006/0190038 A1 | 8/2006 | Carley et al. |
| 2006/0206063 A1 | 9/2006 | Kagan et al. |
| 2006/0207606 A1 | 9/2006 | Roue et al. |
| 2006/0217762 A1 | 9/2006 | Maahs et al. |
| 2006/0235447 A1 | 10/2006 | Walshe |
| 2006/0237022 A1 | 10/2006 | Chen et al. |
| 2006/0237023 A1 | 10/2006 | Cox et al. |
| 2006/0241662 A1 | 10/2006 | Adams et al. |
| 2006/0241691 A1 | 10/2006 | Wilk |
| 2006/0253144 A1 | 11/2006 | Mikkaichi et al. |
| 2006/0271073 A1 | 11/2006 | Lam et al. |
| 2006/0271101 A1 | 11/2006 | Saadat et al. |
| 2007/0010835 A1 | 1/2007 | Breton et al. |
| 2007/0100375 A1 | 5/2007 | Mikkaichi et al. |
| 2007/0100376 A1 | 5/2007 | Mikkaichi et al. |
| 2007/0112362 A1 | 5/2007 | Mikkaichi et al. |
| 2007/0123840 A1 | 5/2007 | Cox |
| 2007/0129755 A1 | 6/2007 | Abbott et al. |
| 2007/0173868 A1 | 7/2007 | Bachinski et al. |
| 2007/0208360 A1 | 9/2007 | Demarais et al. |
| 2007/0219411 A1 | 9/2007 | Dejima et al. |
| 2007/0270752 A1 | 11/2007 | LaBombard |
| 2007/0270943 A1 | 11/2007 | Solem et al. |
| 2007/0276416 A1 | 11/2007 | Ginn et al. |
| 2007/0276424 A1 | 11/2007 | Mikkaichi et al. |
| 2008/0015633 A1 | 1/2008 | Abbott et al. |
| 2008/0086153 A1 | 4/2008 | Sakamoto et al. |
| 2008/0091059 A1 | 4/2008 | Machold |
| 2008/0097489 A1 | 4/2008 | Goldfarb et al. |
| 2008/0114378 A1 | 5/2008 | Matsushita |
| 2008/0114398 A1 | 5/2008 | Phillips et al. |
| 2008/0147116 A1 | 6/2008 | Smith et al. |
| 2008/0154290 A1 | 6/2008 | Golden et al. |
| 2008/0172088 A1 | 7/2008 | Smith et al. |
| 2008/0177304 A1 | 7/2008 | Westra et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228199 A1 | 9/2008 | Cropper et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255423 A1 | 10/2008 | Kondo et al. |
| 2008/0262525 A1 | 10/2008 | Chang et al. |
| 2008/0269566 A1 | 10/2008 | Measamer |
| 2008/0275297 A1 | 11/2008 | Bakos et al. |
| 2008/0281354 A1 | 11/2008 | Cropper et al. |
| 2008/0294178 A1 | 11/2008 | Kortenbach et al. |
| 2008/0296344 A1 | 12/2008 | Cropper et al. |
| 2008/0300547 A1 | 12/2008 | Bakos |
| 2008/0300608 A1 | 12/2008 | Measamer |
| 2008/0300624 A1 | 12/2008 | Schwemberger et al. |
| 2008/0300627 A1 | 12/2008 | Measamer et al. |
| 2008/0319257 A1 | 12/2008 | Sato et al. |
| 2009/0005800 A1 | 1/2009 | Franer et al. |
| 2009/0018552 A1 | 1/2009 | Lam et al. |
| 2009/0069822 A1 | 3/2009 | Takahashi et al. |
| 2009/0088780 A1 | 4/2009 | Shiono et al. |
| 2009/0088797 A1 | 4/2009 | Crombie et al. |
| 2009/0125038 A1 | 5/2009 | Ewers et al. |
| 2009/0125039 A1 | 5/2009 | Mikkaichi et al. |
| 2009/0204147 A1 | 8/2009 | Rahmani |
| 2009/0222029 A1 | 9/2009 | Gordin et al. |
| 2009/0254119 A1 * | 10/2009 | Sibbitt et al. .................. 606/213 |
| 2009/0287080 A1 | 11/2009 | Nishina et al. |
| 2009/0299385 A1 | 12/2009 | Stefanchik et al. |
| 2009/0299406 A1 | 12/2009 | Swain et al. |
| 2009/0306686 A1 | 12/2009 | Ohdaira |
| 2009/0318936 A1 | 12/2009 | Harris et al. |
| 2009/0326578 A1 | 12/2009 | Ewers et al. |
| 2010/0010457 A1 | 1/2010 | Ewers et al. |
| 2010/0010508 A1 | 1/2010 | Takahashi et al. |
| 2010/0010509 A1 | 1/2010 | Ishioka et al. |
| 2010/0010511 A1 | 1/2010 | Harris et al. |
| 2010/0010514 A1 | 1/2010 | Ishioka et al. |
| 2010/0010520 A1 | 1/2010 | Takahashi et al. |
| 2010/0042115 A1 | 2/2010 | Saadart et al. |
| 2010/0042144 A1 | 2/2010 | Bennett |
| 2010/0049244 A1 | 2/2010 | Cohen et al. |
| 2010/0076462 A1 | 3/2010 | Bakos et al. |
| 2010/0076488 A1 | 3/2010 | Spivey et al. |
| 2010/0094341 A1 | 4/2010 | Raju |
| 2010/0106166 A1 | 4/2010 | Cropper et al. |
| 2010/0113873 A1 | 5/2010 | Suzuki et al. |
| 2010/0121351 A1 | 5/2010 | Whitfield et al. |
| 2010/0174312 A1 | 7/2010 | Maahs et al. |
| 2010/0198192 A1 | 8/2010 | Serina et al. |
| 2010/0211086 A1 | 8/2010 | Ewers et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2010/0249498 A1 | 9/2010 | Wingardner et al. |
| 2010/0256658 A1 | 10/2010 | Criscuolo et al. |
| 2010/0264192 A1 | 10/2010 | Marczyk |
| 2010/0268253 A1 | 10/2010 | Ahlberg et al. |
| 2010/0268270 A1 | 10/2010 | Viola |
| 2011/0022065 A1 | 1/2011 | Shipp |

(56) References Cited

U.S. PATENT DOCUMENTS

FOREIGN PATENT DOCUMENTS

| | | |
|---|---|---|
| EP | 1317904 A1 | 11/2003 |
| EP | 1961388 A2 | 8/2008 |
| JP | 2000-514336 | 10/2000 |
| JP | 2010-17542 | 1/2010 |
| WO | WO88/01486 | 3/1988 |
| WO | WO90/02522 | 3/1990 |
| WO | WO95/21575 | 8/1995 |
| WO | WO96/14020 | 5/1996 |
| WO | WO96/40356 | 12/1996 |
| WO | WO 98/02100 | 1/1998 |
| WO | WO98/18389 | 5/1998 |
| WO | WO99/62408 | 12/1999 |
| WO | WO00/07506 | 2/2000 |
| WO | WO00/16701 | 3/2000 |
| WO | WO00/21443 | 4/2000 |
| WO | WO00/56223 | 9/2000 |
| WO | WO00/56227 | 9/2000 |
| WO | WO01/19256 | 3/2001 |
| WO | WO01/35832 | 5/2001 |
| WO | WO01/58363 | 8/2001 |
| WO | WO2005/034729 | 4/2005 |
| WO | WO2007/004228 | 1/2007 |
| WO | WO2007/24615 | 3/2007 |
| WO | WO2007/089843 | 8/2007 |
| WO | WO2007/142977 | 12/2007 |

OTHER PUBLICATIONS

Response to Communication Pursuant to Rules 161(1) and 162EPC for European Patent Application Serial No. 09791618.3, dated May 6, 2011, 4 pages.
International Search Report for PCT/US2009/041415, dated Jul. 24, 2009, 4 pages.
International Preliminary Report on Patentability for PCT/US2009/041415, dated Nov. 4, 2010, 6 pages.
International Search Report for PCT/US2009/054176, dated Nov. 20, 2009, 16 pages.
International Preliminary Report on Patentability for PCT/US2009/054176, dated Mar. 3, 2011, 9 pages.
International Search Report for PCT/US2009/056512, dated Feb. 10, 2010, 5 pages.
Article 34 Demand and Amendment for PCT/US2009/056512, dated Jul. 6, 2010, 22 pages.
International Preliminary Report on Patentability for PCT/US2009/056512, dated Jan. 10, 2010, 31 pages.
International Search Report and Written Opinion for PCT/US2009/056604, dated May 4, 2010, 9 pages.
International Search Report for PCT/US2009/066983, dated Jan. 19, 2010, 4 pages.
International Search Report and Written Opinion for PCT/US2009/066992, dated Mar. 4, 2010, 15 pages.
International Search Report and Written Opinion for PCT/US2009/067992, Jul. 9, 2010, 20 pages.
International Search Report and Written Opinion for PCT/US2009/067994, dated Jun. 10, 2010, 18 pages.
International Search Report and Written Opinion for PCT/US2010/036188, dated Sep. 14, 2010, 18 pages.
Restriction Requirement for U.S. Appl. No. 12/428,226, dated Apr. 27, 2011, 7 pages.
Response to Restriction Requirement for U.S. Appl. No. 12/428,226, dated May 27, 2011, 10 pages.
Office Action for U.S. Appl. No. 12/428,226, dated Jun. 9, 2011, 8 pages.
Office Action for U.S. Appl. No. 12/543,000, dated Mar. 15, 2011, 14 pages.
Fritscher-Ravens, "Transgastric endoscopy—a new fashion, a new excitement!", *Endoscopy*, vol. 39, 2007, pp. 161-167.
Sporn et al., "Endoscopic colotomy closure after full thickness excision: comparison of T fastener with mutliclip applier",*Endoscopy*, vol. 40, 2008, pp. 589-594.
Voermans et al., "In vitro comparison and evaluation of seven gastric closure modalities for natural orifice transluminal endoscopic surgery", *Endoscopy*, vol. 40, 2008, pp. 595-601.
Sclabas et al., "Endoluminal Methods for Gastrotomy Closure in Natural Orifice TransEnteric Surgery", *Surgical Innovation*, vol. 13, No. 1, Mar. 2006, pp. 23-30.
Desilets et al., "Loop-anchor purse-string versus endoscopic clips for gastric closure: a natural orifice transluminal endoscopic surgery comparison study using burst pressures", *Gastrointestinal Endoscopy*, vol. 70, No. 6, 2009, pp. 1225-1230.
Sporn et al., "Endoscopic colotomy closure for natural orifice transluminal endoscopic surgery using a T-fastener protoype in comparison to conventional laparoscopic suture closure", *Gastrointestinal Endoscopy*, vol. 68, No. 4, 2008, pp. 724-730.
Dray et al., "Air and fluid leak tests after NOTES procedures: a pilot study in a live porcine model ", *Gastrointestinal Endoscopy*, vol. 68, No. 3, 2008, pp. 513-519.
Shurr et al., "An over-the-scope clip (OTSC) system for closure of iatrogenic colon perforations: results of an experimental survival study in pigs", *Endoscopy*, vol. 40, 2008, pp. 584-588.
Romanelli et al, "Natural orifice transluminal endoscopic surgery gastrotomy closure in porcine explants with the Padlock-G clip using the Lock-It system", *Endoscopy*, vol. 42, 2010, pp. 306-310.
Bergström et al., "Early clinical experience with a new flexible endoscopic suturing method for natural orifice transluminal endoscopic surgery and intraluminal endosurgery", *Gastrointestinal Endoscopy*, vol. 67, No. 3, 2008, pp. 528-533.
Park et al, "Endoscopic sutured closure of a gastric natural orifice transluminal endoscopic surgery access gastronomy compared with open surgical closure in a porcine model. A randomized, multicenter controlled trial", *Endoscopy*, vol. 42, 2010 pp. 311-317.
Yasser M. Bhat, MD, "Transluminal Endosurgery: Novel Use of Endoscopic Tacks for the Closure of Access Sites in Natural Orifice Transluminal Endoscopic Surgery," *Gastrointestinal Endoscopy*, vol. 69, No. 6, p. 1161.
International Preliminary Report on Patentability for PCT/US2010/036188 dated Dec. 8, 2011, 10 pgs.
Communication Under Rules 161(1) and 162 EPC for European Patent Application 10726736.1 dated Jan. 30, 2012, 2 pgs.
Reply to Communication Under Rules 161(1) and 162 EPC for European Patent Application 10726736.1 dated Jul. 30, 2012, 13 pgs.
Communication Under Article 94(3) EPC for European Patent Application 10726736.1 dated Apr. 4, 2013, 4 pgs.
Office Action for Canadian Application 2,763,133 dated Oct. 1, 2013, 3 pgs.
Examination Report No. 1 for Australian Application 2010254151 dated Nov. 19, 2012, 3 pgs.
Reply to Examination Report No. 1 for Australian Application 2010254151 dated Jul. 16, 2013, 7 pgs.
Examination Report No. 2 for Australian Application 2010254151 dated Sep. 23, 2013, 3 pgs.
Reply to Examination Report No. 2 for Australian Application 2010254151 dated Nov. 13, 2013, 4 pgs.
Notice of Acceptance for Australian Application 2010254151 dated Nov. 19, 2013, 2 pgs.
Office Action dated Feb. 12, 2014 for Japanese Patent Application 2012-513205, 5 pgs. Including English translation.
Office Action dated Nov. 18, 2014 for Japanese Patent Application 2012-513205, 3 pgs. Including English translation.

\* cited by examiner

TACKING DEVICE AND METHODS OF DEPLOYMENT

PRIORITY CLAIM

This invention claims the benefit of priority of U.S. Provisional Application Ser. No. 61/181,946, entitled "Tacking Device and Methods of Deployment," filed May 28, 2009, the disclosure of which is hereby incorporated by reference in its entirety.

BACKGROUND

The present embodiments relate generally to medical devices, and more particularly, to apparatus and methods for coupling a graft member to tissue, closing a bodily opening, and the like.

Perforations in tissue or bodily walls may be formed intentionally or unintentionally. For example, an unintentional ventral abdominal hernia may be formed in the abdominal wall due to heavy lifting, coughing, strain imposed during a bowel movement or urination, fluid in the abdominal cavity, or other reasons. Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been attempted by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation.

In order to secure the graft material to the surrounding tissue, sutures commonly are manually threaded through the full thickness of the surrounding tissue. In the case of a ventral abdominal hernia, the sutures may be threaded through the thickness of the abdominal wall, then tied down and knotted. However, such manual suturing techniques may be time consuming and/or difficult to perform.

In addition to covering and sealing perforations, there are various other instances in which it may be desirable to couple a graft material to tissue. For example, it may become necessary or desirable to couple the graft material to a region of tissue for purposes of reconstructing the local tissue. Whether a graft material is coupled to tissue to reconstruct local tissue, seal a perforation, or another purpose, it would be desirable to provide apparatus and methods for quickly and effectively coupling the graft material to the tissue.

Various tacking devices have been used to couple a graft to tissue during hernia procedures. Some of the tacking devices comprise spiral or threaded members. In some cases, a screwdriver may engage a head region of the tacking device to screw the tacking device into the tissue, or alternative, loosen its engagement with the tissue. However, such tacking devices comprise rigid members having a fixed profile, which therefore requires a relatively large delivery device and incision. Moreover, the inventor has discovered that tacking devices may permit slipping of the graft member relative to the tissue, and the head region may significantly protrude into a body space and inadvertently snag on organs such as the intestines, causing surgical complications.

SUMMARY

The present embodiments provide a tacking device for engaging tissue, which may be useful for coupling a graft to tissue, facilitating closure of a bodily opening, and the like. In one embodiment, the tacking device comprises a wire having first and second ends, and further having delivery and deployed states. In the delivery state, the wire comprises an elongated configuration that is substantially parallel to a central longitudinal axis. In the deployed state, the wire comprises a head region and a body region, the head region comprising at least one full turn having a first diameter, and the body region comprising at least two full turns having a second diameter.

The first diameter of the full turn of the head region may be greater than the second diameter of the at least two full turns of the body region. Further, a longitudinal distance of the body region may be at least three times greater than a longitudinal distance of the head region. The wire of the tacking device may comprise a nickel-titanium alloy that is configured to self-expand from the delivery state to the deployed state.

A tacking device provided in accordance with the present embodiments may be used to treat an array of medical conditions. For example, when used to couple a graft member to tissue to treat a ventral hernia, the at least one full turn of the head region may abut the graft member, while the at least two full turns of the body region may engage the tissue.

The tacking device may be delivered within a hollow lumen of an insertion tool in the delivery state, and may be deployed using multiple techniques. For example, a laparoscopic delivery technique may be used in which the insertion tool is advanced through a laparoscopic device and the body region of the wire is deployed prior to the head region. Alternatively, an endoscopic delivery technique may be used in which the insertion tool is advanced through a lumen of an endoscope and the body region of the wire is deployed prior to the head region. Still further, a percutaneous delivery technique may be used in which the insertion tool is advanced directly through abdominal skin and the head region of the wire is deployed prior to the body region. In any of the above techniques, multiple tacking devices may be loaded in a sequential manner within the hollow lumen of the insertion tool, and then sequentially deployed to secure the graft member to the tissue at multiple different locations.

Advantageously, in the deployed state, the design of the head region of the tacking device may reduce the risk of complications such as inadvertent snagging on the intestines. Moreover, the enlarged diameter of the head region may reduce the likelihood of the graft member slipping off the tacking device and away from the tissue. Still further, since the tacking device can be delivered as an elongated wire in the delivery state, the profile of the insertion tool and bodily incision may be reduced.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure. Thus, "proximal" and "distal" portions of a device or bodily region may depend on the point of entry for the procedure (e.g., percutaneously versus endoscopically).

Figure 1A:
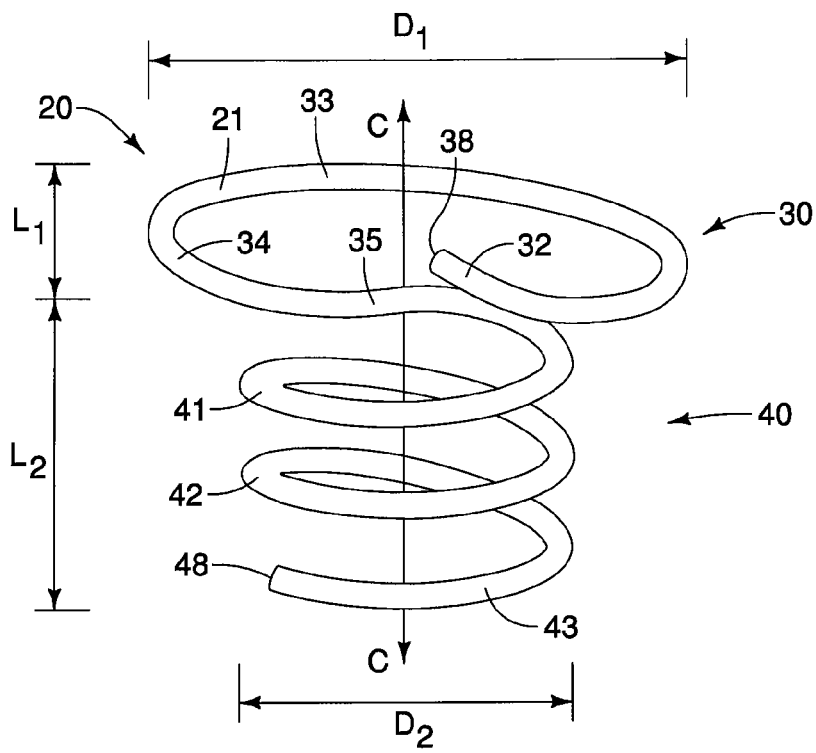
FIGS. 1A-1B illustrate a side view of a tacking device from a slightly elevated perspective, and a top view, respectively.
Figure 1B:
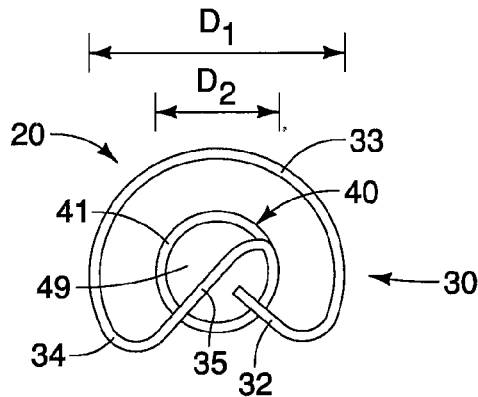
Figure 2:
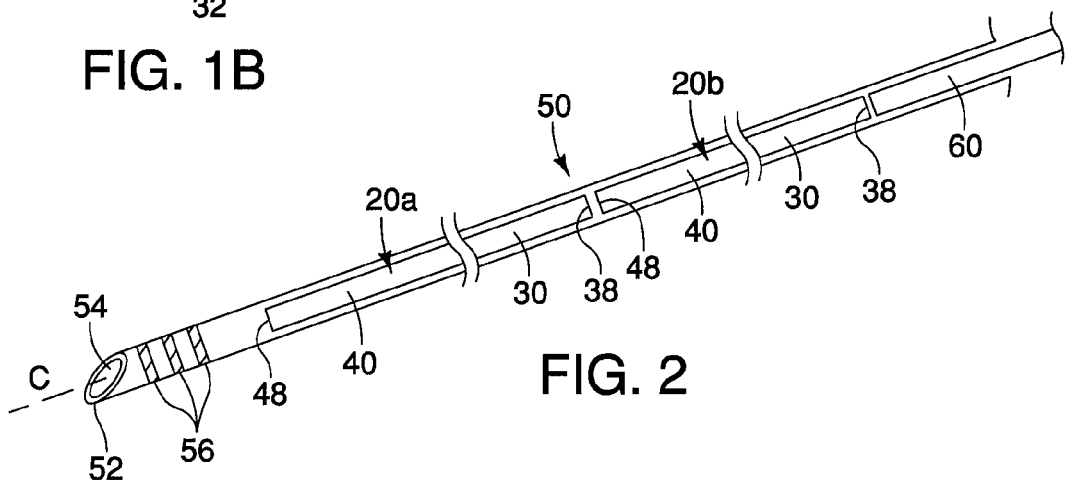
FIG. 2 is a perspective, cut-away view illustrating multiple tacking devices in a delivery configuration within an insertion tool.

Referring now to FIGS. 1A-1B, a first embodiment of a tacking device 20 is shown in a deployed or expanded state. The tacking device 20 comprises a single wire 21 having first and second ends 38 and 48. As used herein, the term "wire" refers to a generally wire-like member, and is not limited to a metal member, but rather may include plastic or any other material. In the expanded state of FIGS. 1A-1B, the wire 21 comprises a head region 30 and a body region 40, and has a series of turns through both regions, as described in further detail below. For reference purposes, the tacking device 20 has a central longitudinal axis C, as illustrated in FIGS. 1-2.

The head region 30 generally extends from the first end 38 towards a junction 35, which separates the head region 30 from the body region 40. The first end 38 may be positioned such that it intersects with, or is adjacent to, the central longitudinal axis C, and may transition into a substantially straight segment 32 that extends in a radially outward direction away from the central longitudinal axis C. The substantially straight segment 32 then transitions into a curved segment 33, which preferably spans at least 360 degrees and terminates at the junction 35, as depicted in FIGS. 1A-1B.

The junction 35 may comprise a single point, or may comprise a short straight segment delineating a transition between the first and second regions 30 and 40. The junction 35 may effectively change the direction of curvature of the wire 21. For example, as shown in FIGS. 1A-1B, while the wire 21 extends in a generally counterclockwise direction through the head region 30, the junction 35 changes the direction so that the wire 21 extends in a clockwise direction through the body region 40.

In the exemplary embodiment of FIGS. 1A-1B, the curved segment 33 spans about 450 degrees, i.e., one full counterclockwise turn of 360 degrees, plus 90 additional degrees. More particularly, as shown in FIGS. 1A-1B, there is a portion 34 along the curved segment 33 that is parallel to the substantially straight segment 32, thereby indicating a curvature of 360 degrees, and the wire 21 further extends about another 90 degrees from the portion 34 to the junction 35. Accordingly, in this example, the junction 35 is oriented approximately orthogonal to the substantially straight segment 32, as depicted in FIGS. 1A-1B. The junction 35 may extend laterally in a direction that intersects with, or nearly coincides with, a line defined by the central longitudinal axis C. The junction 35 therefore may be longitudinally and/or radially offset from the first end 38 of the wire 21, so that the junction 35 does not interfere with the first end 38 in the expanded state.

The curved segment 33, while not necessarily forming a perfectly enclosed circle, comprises a diameter $D_1$, which may be defined as the maximum straight line extension away from the central longitudinal axis C, as depicted in FIGS. 1A-1B. As will be explained in further detail below, an increased diameter $D_1$ may enhance an engagement between the head region 30 and a graft member covering a perforation in tissue to thereby reduce the likelihood of the graft member slipping off the tacking device 20 and away from the tissue.

While the curved segment 33 is shown spanning approximately 450 degrees, the curved segment 33 may span a shorter or greater length. For example, the curved segment may extend in a counterclockwise direction through at least two full turns of 360 degrees or more. It may be noted, however, that by utilizing fewer than two full turns, a longitudinal distance $L_1$ of the head region 30 may be reduced, which advantageously may reduce protrusion of the head region 30 into the peritoneum during treatment of a ventral hernia, as explained further below.

Referring still to FIG. 1A, the body region 40 generally extends from the junction 35 towards the second end 48. As noted above, the junction 35 may change the direction of the wire to cause the body region 40 to extend in a clockwise direction. In the exemplary embodiment of FIG. 1A, the body region 40 comprises at least two full turns 41 and 42, each of which span 360 degrees. A partial turn 43 of less than 360 degrees extends between the full turn 42 and the second end 48 of the wire 21. However, the body region 40 may span two full turns or less, or alternatively, three full turns or more. Notably, the diameter $D_2$ of the turns 41 and 42 of the body region 40 is smaller than the diameter $D_1$ of the head region 30. The ratio of the diameter $D_1$ to the diameter $D_2$ may be about 2 to 1, although an increased or reduced ratio may be provided.

In the embodiment shown, the body region 40 defines a cylindrical shape in the deployed state in which the diameter $D_2$ of each of the turns is approximately equal. However, in an alternative embodiment, the diameter of the turn 41 may be larger than the diameter of the turn 42, such that the body region 40 tapers in a screw-like manner.

The at least two full turns 41 and 42 of the body region 40 rotate around the central longitudinal axis C, forming an interior space 49 therein, as shown in FIG. 1B. A portion of the head region 30 also rotates around the interior space 49, as shown in FIG. 1B. The junction 35 may extend through the interior space 49, longitudinally between the first and second regions 30 and 40, to effectively change the direction of curvature of the wire 21.

Based in part on the number of turns, as well as the diameter $D_2$ of the turns, the body region 40 spans a longitudinal distance $L_2$, as depicted in FIG. 1A. The number of full turns may be selected based on the particular medical application. For example, during treatment of a ventral hernia, the number of turns along the body region 40 may be selected such that the body region 40 is disposed substantially within abdominal tissue, as explained further below. Moreover, the longitudinal distances $L_1$ and $L_2$, accounting for the entire longitudinal length of the tacking device 20, may be dimensioned to be substantially equal to or less than the combined thickness $t_1$ and $t_2$ of a tissue 74 and a graft member 80, respectively, as shown in the examples below.

In a preferred embodiment, the longitudinal distance $L_2$ of the body region 40 is at least three times greater than the longitudinal distance $L_1$ of the head region 30. However, the longitudinal distance $L_2$ may range from about 1.5 to about 10.0 times greater than the longitudinal distance $L_1$. Advantageously, a relatively short longitudinal distance $L_1$ of the head region 30 may reduce protrusion of the tacking device 20 into a body space such as the peritoneum, while a relatively long longitudinal distance $L_2$ of the body region 40 may increase engagement with the tissue 74.

In addition to the expanded deployed state shown in FIGS. 1A-1B, the tacking device 20 comprises a contracted or delivery state, as shown in FIG. 2. In a preferred embodiment, the wire 21 of the tacking device 20 comprises a shape-memory material, such as a nickel-titanium alloy (nitinol). If a shape-memory material such as nitinol is employed, the wire 21 may be manufactured such that it can assume the preconfigured expanded state shown in FIGS. 1A-1B upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature ($M_f$) to the martensitic phase and then deformed to a second configuration. Upon heating to another transformation temperature ($A_f$), the material may spontaneously return to its initial, predetermined configuration, as shown in FIGS. 1A-1B. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the wire 21 may be made from other metals and alloys that are biased, such that they may be restrained prior to deployment, but are inclined to return to their relaxed, expanded configuration upon deployment. Solely by way of example, the wire 21 may comprise other materials such as stainless steel, cobalt-chrome alloys, amorphous metals, tantalum, platinum, gold and titanium, or may be made from non-metallic materials, such as thermoplastics and other polymers.

As shown in FIG. 2, the wire 21 of the tacking device 20 comprises an elongated configuration in the contracted state, i.e., the wire 21 is oriented along the central longitudinal axis C. In this state, one or more tacking devices 20 may be delivered to a target site in a patient's anatomy using an insertion tool 50. In one embodiment, the insertion tool 50 is capable of carrying multiple different tacking devices, such as first and second tacking devices 20a and 20b, as shown in FIG. 2 and described below.

In one embodiment, the insertion tool 50 comprises a needle-like body having a sharpened distal tip 52 and a hollow lumen 54. The insertion tool 50 may be manufactured from stainless steel or any other suitable material, and may comprise an endoscopic ultrasound (EUS), or echogenic, needle. Solely by way of example, the insertion tool 50 may comprise the EchoTip® Ultrasound Needle, or the EchoTip® Ultra Endoscopic Ultrasound Needle, both manufactured by Cook Endoscopy of Winston-Salem, N.C.

The hollow lumen 54 of the insertion tool 50 may comprise an inner diameter than is larger than an outer diameter of the wire 21 forming the tacking devices. Therefore, the first and second tacking devices 20a and 20b may be loaded into the hollow lumen 54 of the insertion tool 50 in a sequential manner, as shown in FIG. 2. The direction of loading of the wires 21 is important and may be determined based on the procedure and associated entry point, e.g., laparoscopic versus percutaneous, as described greater below. In FIG. 2, the loading of the first and second tacking devices 20a and 20b is suitable for a laparoscopic or endoscopic procedure, wherein the body region 40 is deployed prior to the head region 30. Accordingly, the second end 48 of the first tacking device 20a may be closest to the sharpened distal tip 52 of the insertion tool 50, while the first end 38 of the first tacking device 20a may abut the second end 48 of the second tacking device 20b, as depicted in FIG. 2.

A stylet 60 may be disposed for longitudinal movement within the hollow lumen 52 of the insertion tool 50, as shown in FIG. 2. The stylet 60 may comprise stainless steel or any other suitable material. The stylet 60 is disposed proximal to the second, or final, tacking device 20b. During use, the insertion tool 50 may be proximally retracted, while the stylet 60 may be held longitudinally steady, to facilitate sequential deployment of the first and second tacking devices 20a and 20b, as explained further below.

Figure 3:
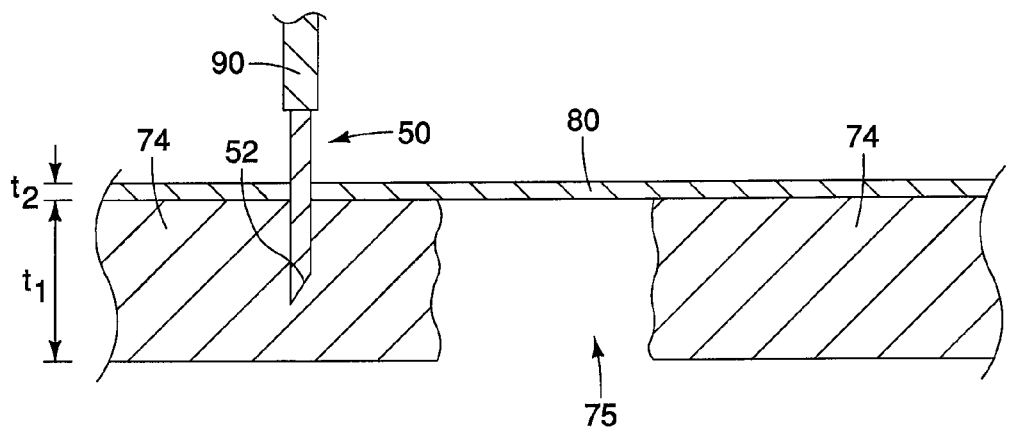
FIGS. 3-5 are side-sectional views illustrating an exemplary laparoscopic deployment of one or more of the tacking devices of FIGS. 1-2 to treat a ventral hernia.

The insertion tool 50 may comprise one or more markers 56, as shown in FIG. 2, which may be disposed near the distal end of the insertion tool 50. The markers 56 may be configured to be visualized under fluoroscopy of other imaging techniques to facilitate location of the distal end of the insertion tool, for example, so that a physician may determine how far the insertion tool 50 has penetrated into tissue 74, as depicted in FIG. 3 below. As will be explained further below, the insertion tool 50 may be used in conjunction with another device, such as a laparoscopic device or an endoscope.

The dimensions of the tacking device 20 may be tailored based on a particular surgical procedure, a particular patient's anatomy and/or other factors. Advantageously, since the tacking device 20 can be delivered as an elongated wire prior to deployment into the shape of FIGS. 1A-1B, the overall profile of the insertion tool may be reduced, which may result in a smaller incision.

Figure 4:
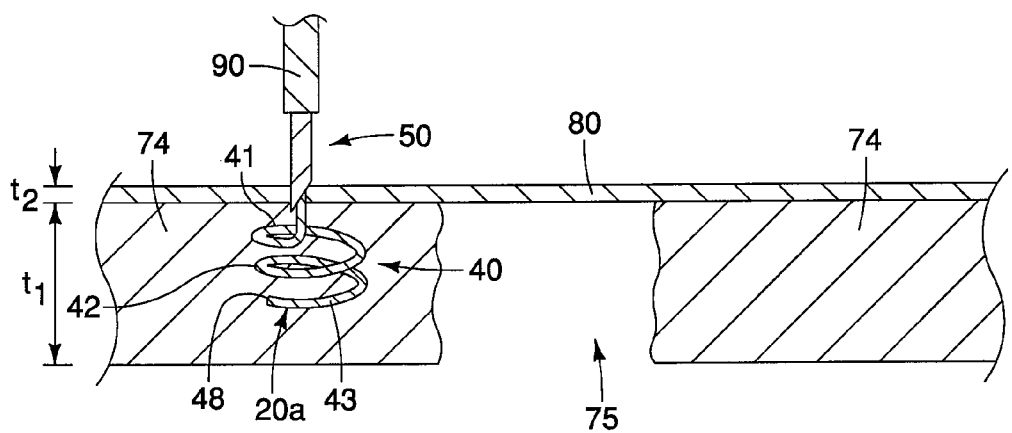
Figure 5:
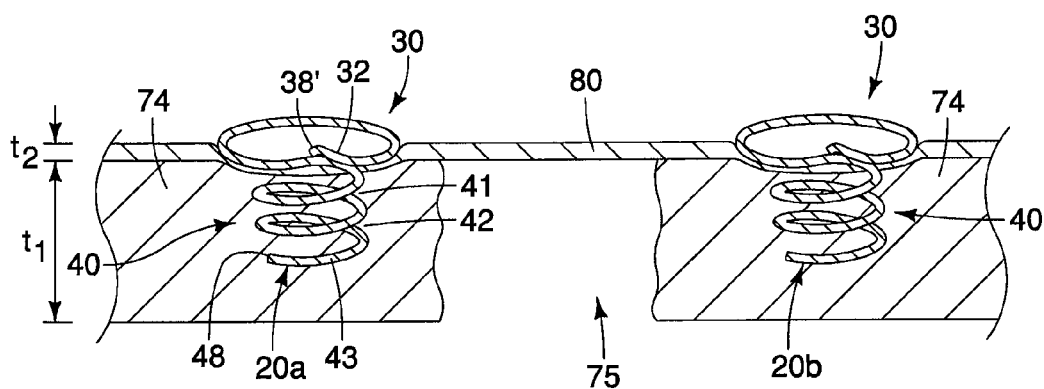

Referring now to FIGS. 3-5, one or more tacking devices 20 described above may be used to facilitate treatment of a perforation 75 using a graft member 80. In the example shown, the perforation 75 is a ventral hernia located in the tissue 74 of the abdominal wall. While treatment of a ventral hernia is shown for illustrative purposes, it will be apparent that the tacking devices described herein may be used in a wide range of medical procedures, including but not limited to any exemplary procedures described herein.

The initial stages of the ventral hernia repair may be performed using techniques that are known. In the example of FIGS. 3-5, a laparoscopic technique is employed whereby multiple relatively small incisions are made to access the hernia site. A first laparoscopic device (not shown) may be used to visualize the peritoneum, while a second laparoscopic device 90 may be used to deliver the insertion tool 50.

The graft member 80 may comprise any suitable material for covering the perforation 75 and substantially or entirely inhibiting the protrusion of abdominal matter. In one embodiment, the graft member 80 may comprise small intestinal submucosa (SIS), such as SURGISIS® BIODESIGN™ Soft Tissue Graft, available from Cook Biotech, Inc., West Lafayette, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. Preferably, the graft member 80 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The graft member 80 may also comprise a composite of a biomaterial and a biodegradeable polymer. Additional details may be found in U.S. Pat. No. 6,206,931 to Cook et al., the disclosure of which is incorporated herein by reference in its entirety.

Referring now to FIG. 3, after the graft member 80 has been placed to cover the perforation 75 using known techniques, the laparoscopic device 90 may be maneuvered into a desired position within the peritoneum. The distal end of the laparoscopic device 90 may be positioned facing the graft member 80, as shown in FIG. 3. In a next step, the insertion tool 50 may be advanced distally through a lumen of the laparoscopic device 90 to pierce through the graft member 80, and further may pierce at least partially into the tissue 74 at a first location around the perimeter of the perforation 75.

In this example, the insertion tool 50 is carrying two sequential tacking devices 20a and 20b, which may be disposed within the hollow lumen 54 of the insertion tool 50 as shown in FIG. 2 above. With the tacking devices 20a and 20b in the contracted delivery states, the sharpened tip 52 of the insertion tool 50 may be advanced to a predetermined depth into the tissue 74. The markers 56 of FIG. 2 may facilitate in determining how far the insertion tool 50 has penetrated into the tissue 74.

In a next step, the stylet 60 of FIG. 2 may be held steady with respect to the insertion tool 50, while the insertion tool 50 is retracted in a proximal direction, i.e., away from the tissue 74 and towards the peritoneum. This causes the second end 48 of the most distal tacking device 20a to extend distal to the sharpened tip 52 of the insertion tool 50, and causes a progressive deployment of the partial turn 43, followed by the second full turn 42 and the first full turn 41 of the body region 40, as depicted in FIG. 4. When the body region 40 of the wire 21 is no longer radially constrained by the insertion tool 50, the partial turn 43 and full turns 41 and 42 may assume their predetermined expanded configurations in which they may engage the tissue 74. Preferably, the partial turn 43 and full turns 41 and 42 become embedded or interwoven with the tissue 74, e.g., the tissue may fill the open spaced between the turns of the wire 21, thereby securing the body region 40 within the tissue 74.

As the insertion tool 50 further is retracted proximally with respect to the first tacking device 20a, the head region 30 may assume its predetermined expanded configuration when no longer radially constrained, as shown in FIG. 5. In the expanded configuration, the head region 30 may engage or abut the graft member 80. In this manner, the tacking device 20a helps secure the graft material 80 against the tissue 74.

In an alternative deployment technique, the stylet 60 may be distally advanced, while the insertion tool 50 is held steady, to distally advance the first tacking device 20a relative to the insertion tool 50. Still further, the stylet 60 may be distally advanced while the insertion tool 50 is proximally retracted to deploy the first tacking device 20a. Using either technique, the tacking device 20a itself may be visualized using a desired modality, such as fluoroscopy, and in particular the junction 35.

After the first tacking device 20a has been deployed, the insertion tool 50 may be repositioned to deploy the second tacking device 20b around the perimeter of the perforation 75. The second tacking device 20b may be deployed in the same manner as the first tacking device 20a. In this manner, multiple tacking devices may secure the graft member 80 around the perimeter of the perforation 75, as shown in FIG. 5. As will be apparent, greater than two tacking devices may be used, and the positioning of the tacking devices may be varied to optimize securing the graft member 80 to the tissue 74 in order to substantially seal the perforation 75.

Advantageously, since the longitudinal distance $L_1$ of the head region 30 is relatively small, the head region 30 provides a relatively flat surface that may reduce protrusion of the tacking devices 20 into the peritoneum, as depicted in FIG. 5. Moreover, the head region 30 does not comprise any substantially sharp surfaces that can inadvertently snag on, or pierce through, bodily organs such as the intestines. If desired, an alternative first end 38' of the head region 30 may be bent inward, i.e., towards the tissue 74 and the second end 48, as shown in FIG. 5, to further reduce complications such as inadvertent snagging of the tacking device 20. Further, the enlarged diameter $D_1$ of the head region 30 provides an enhanced surface contact with the graft member 80, which may reduce the likelihood of the graft member 80 falling off the tacking device 20 and slipping away from the tissue 74.

Optionally, the laparoscopic device 90 may be periodically pushed distally to abut the graft member 80 as the insertion tool 50 is retracted proximally to deploy the head region 30. This technique may help ensure that the head region 30 is deployed entirely proximal to the graft member 80, thereby sandwiching the graft member 80 between the head region 30 and the body region 40. Alternatively, a blunt outer sheath may be advanced over the insertion tool 50, via the annular space between the laparoscopic device 90 and the insertion tool 50, to push against the tissue 74 as needed during deployment.

In a further alternative embodiment, where multiple tacking devices 20a and 20b are sequentially positioned around the perforation 75 in a semi-annular or annular shape, a suture may be disposed between the multiple tacking devices. For example, the suture may be looped under or around the head regions 30 of the first and second tacking devices 20a and 20b, with first and second ends of the suture being capable of manipulation by a physician. The first and second ends of the suture then may be tensioned in a purse-string manner to reduce the distance between the tacking devices and compress the tissue 74 around the perforation 75. The suture ends may be secured to maintain the compression of the tissue 74 using any suitable technique such as by forming a knot or using clamps, rivets and the like.

Figure 6:
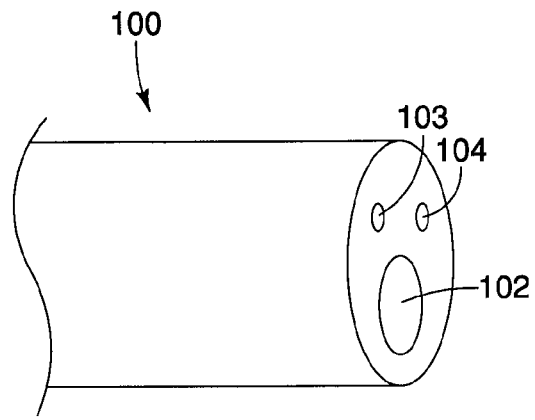
FIG. 6 is a perspective view of the distal region of an exemplary end-viewing endoscope.
Figure 7:
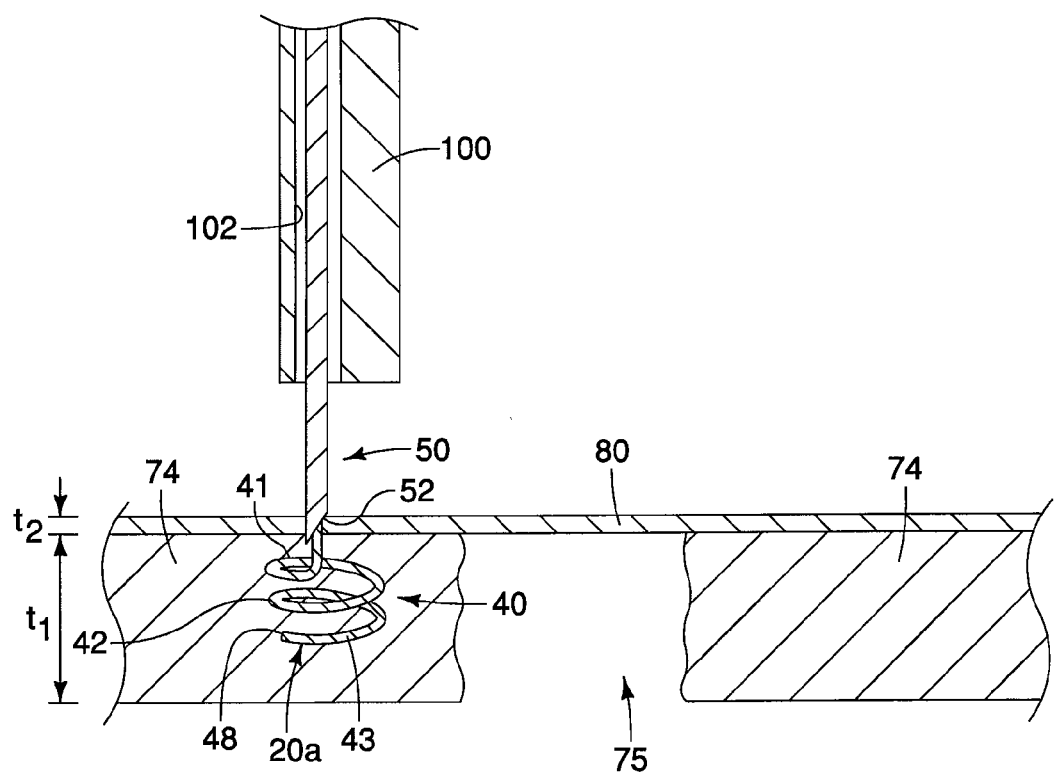
FIG. 7 is a side-sectional view illustrating an endoscopic approach for treatment of a ventral hernia using one or more of the tacking devices of FIGS. 1-2.

Referring now to FIGS. 6-7, an endoscopic approach for treatment of a ventral hernia is described. The endoscopic approach is similar to the laparoscopic approach described in FIGS. 3-5 above, however, an endoscope 100 is used instead of the laparoscopic devices, and no visible incisions may be made on the skin of the patient. In particular, the endoscope 100 may be advanced through a bodily lumen such as the alimentary canal, with an access hole being created through the alimentary canal, to obtain peritoneal access to the ventral hernia, as depicted in FIG. 7.

One or more components, such as the insertion tool 50, may be advanced through a working lumen 102 of the endoscope. The distal end of the insertion tool 50 may be viewed via optical elements 103 and 104 of the endoscope 100, which may comprise fiber optic components for illuminating and capturing an image distal to the endoscope 100. Under suitable visualization using a light source and an eyepiece, a physician may deploy multiple tacking devices one at one time using the insertion tool 50.

If this endoscopic approach is employed, the insertion tool 50 may carry additional tacking devices 20 to subsequently close the access hole in the alimentary canal. Specifically, a first set of multiple tacking devices 20 may be used to secure the graft member 80 to the tissue 74, as described in detail in FIGS. 3-5 above, and then a second set of multiple tacking devices 20 may be used to facilitate closure of the access opening in the alimentary canal, with or without use of a graft member. It should be noted that while only one specific endoscopic deployment step is shown in FIG. 7, the other steps are shown and described in FIGS. 3-5 above, and the final deployment of the tacking devices 20*a* and 20*b* using an endoscopic approach will be substantially the same as depicted in FIG. 5 above.

Figure 8:
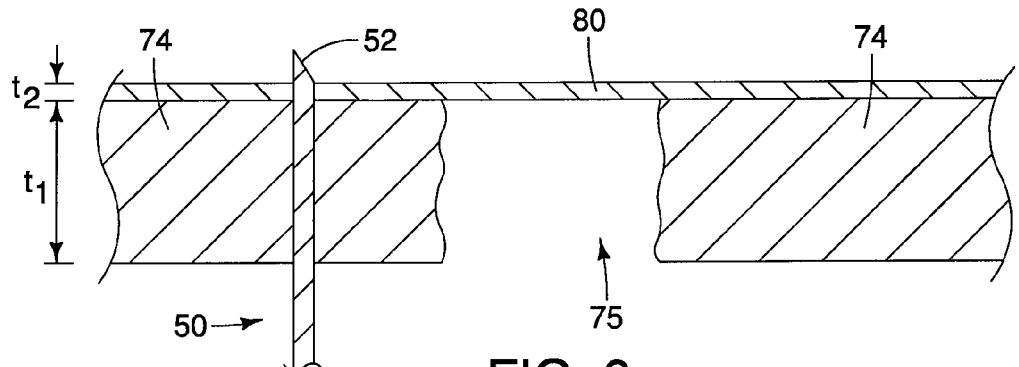
FIGS. 8-10 are side-sectional views illustrating a percutaneous deployment of one or more of the tacking devices of FIGS. 1-2 to treat a ventral hernia.
Figure 9:
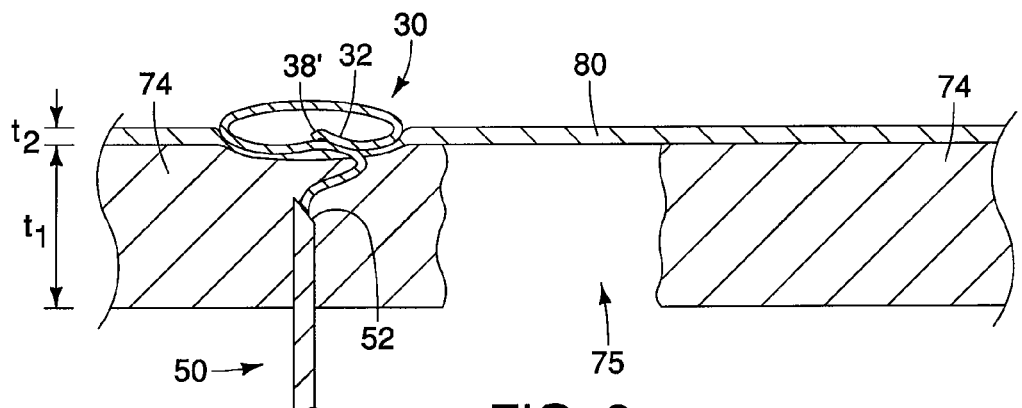
Figure 10:
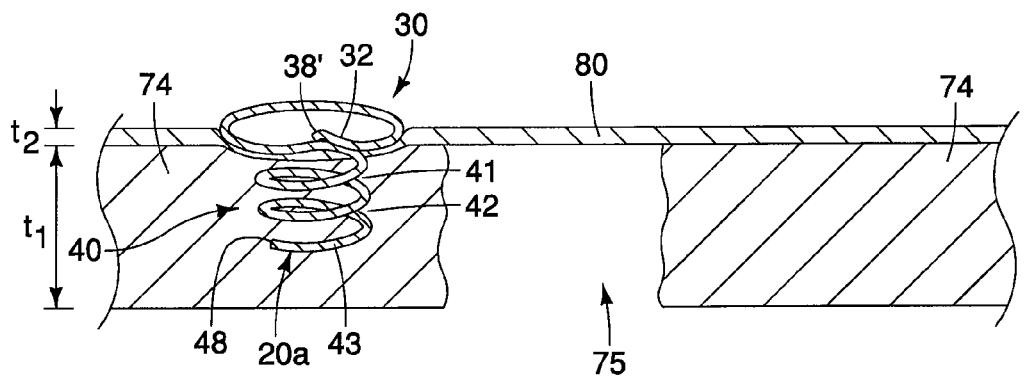

Referring now to FIGS. 8-10, a percutaneous approach for treatment of a ventral hernia is described. The percutaneous approach is similar to the laparoscopic approach described in FIGS. 3-5 above, but with some notable differences. First, in the percutaneous technique, then insertion tool 50 is advanced in a direction from the abdominal tissue 74 towards the graft member 80. Accordingly, the head region 30 is deployed prior to the body region 40, as explained below. Further, the insertion tool 50 may be advanced directly through a patient's abdominal skin.

If a percutaneous approach is used, the tacking devices 20 must be loaded in an opposite direction within the insertion tool 50, relative to loading for the laparoscopic and endoscopic approaches described above. More particularly, referring to FIG. 2 above, in a percutaneous approach the first end 38 of the head region 30 of the first tacking device 20*a* would be located closest to the sharpened tip 52 of the needle. Further, the second end 48 of the first tacking device 20*a* would abut the first end 38 of the second tacking device 20*b*, and the stylet 60 would abut the second end 48 of the second tacking device 20*b*.

With the components loaded as described, the insertion tool 50 then is advanced directly through a patient's abdominal skin, through the tissue 74, and may be advanced just distal to the graft member 80 into the peritoneum, as shown in FIG. 8. In order to optimally visualize the insertion tool 50, a laparoscopic viewing device may be positioned in the peritoneum, or an endoscope may be translumenally advanced in proximity to the target site, as noted in the embodiments above. Alternatively, the insertion tool 50, and markers 56 in particular, may be viewed using fluoroscopy of other suitable techniques.

In a next step, the stylet 60 of FIG. 2 may be held steady with respect to the insertion tool 50, while the insertion tool 50 is retracted in a proximal direction, i.e., away from the peritoneum and towards the tissue 74. This causes the first end 38 of the first tacking device 20*a* to extend distal to the sharpened tip 52 of the insertion tool 50, and causes the head region 30 to be deployed. By aligning the sharpened tip 52 of the insertion tool 50 with the graft member 80, the head region 30 may be deployed into abutting contact with the graft member 80, as shown in FIG. 9. As the insertion tool 50 further is retracted proximally with respect to the first tacking device 20*a*, the first full turn 41 of the body region 40 is deployed, followed by the second full turn 42 and the partial turn 43. As noted above, in the expanded state, the full turns 41 and 42 and the partial turn 43 may become embedded or interwoven with the tissue 74, thereby securing the body region 40 into the tissue 74. After the first tacking device 20*a* has been deployed, the insertion tool 50 may be repositioned to deploy additional tacking devices around the perimeter of the perforation 75, as generally described above.

As noted above, in an alternative embodiment, the diameter of the turn 41 may be larger than the diameter of the turn 42, such that the body region 40 tapers in a screw-like manner. In a further alternative embodiment, there may be multiple relatively large diameter turns separated by multiple relatively small or intermediate diameter turns. For example, from the head region towards the body region, there may be a relatively large turn, followed by a relatively small turn, followed by a relatively large turn, followed by an intermediate turn, and followed by a relatively small turn. Several different such combinations of diameter turns are possible. Moreover, in yet a further alternative embodiment, the tacking device may comprise a uniform helical diameter throughout its entire longitudinal length.

While the exemplary embodiments herein have illustrated the use of one or more tacking devices 20 for covering a perforation 75 formed in the ventral abdominal wall, the tacking devices disclosed herein may be useful in many other procedures. Solely by way of example, one or more tacking devices 20 may be used to treat perforations in a visceral wall, such as the stomach wall. Further, the tacking devices 20 may be used to secure a graft member to tissue for reconstructing local tissue, and the like.

In yet further applications within the scope of the present embodiments, the tacking devices 20 need not be used for coupling a graft member to tissue. For example, the tacking devices 20 may be used in an anastomosis procedure. In order to create an anastomosis, for example, multiple tacking devices 20 may be deployed in a circular manner to couple a proximal vessel, duct or organ to a distal vessel, duct or organ. In such cases, a suitable insertion device, such as an endoscope, may be advanced through a bodily lumen such as the alimentary canal to a position proximate the target location. One or more components, such as the insertion tool 50, may be advanced through a working lumen of the endoscope. The distal end of the insertion tool 50 may be viewed under fluoroscopy, or via optical elements of the endoscope, or by some other visualization technique. Under suitable visualization, multiple tacking devices then may be delivered at one time, for example, using the insertion tool 50. Then, a hole may be punched through the middle of the deployed tacking devices to create a flow path between the proximal and distal vessels/ducts/organs.

It will be apparent that still further applications of the tacking devices 20 are possible. Finally, while exemplary laparoscopic, endoscopic and percutaneous delivery techniques have been described, it should be noted that one or more tacking devices 20 described herein may be deployed at a target site during an open medical procedure.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A tacking device comprising:
    a wire having first and second ends, and further having delivery and deployed states,
    wherein, in the delivery state, the wire comprises an elongated configuration that is substantially parallel to a central longitudinal axis,
    wherein, in the deployed state, the wire comprises a head region, a body region and a junction disposed therebetween, the head region comprising a curved portion substantially within a plane, a first diameter, and a substantially straight segment adjacent to the first end wherein the first end is bent in a direction towards the second end and terminates adjacent to the plane in the deployed state, and the body region comprising at least two full turns having a second diameter,
    wherein the first diameter is greater than the second diameter, wherein the junction changes a direction of curvature of the wire from clockwise to counterclockwise directions,
    wherein a turn of the first diameter leads into the junction, and
    wherein, in the deployed state, there is a curvature in one direction only along the head region, and the junction is substantially straight.

2. The tacking device of claim 1 wherein a longitudinal distance of the body region is at least three times greater than a longitudinal distance of the head region in the deployed state.

3. The tacking device of claim 1 wherein the first diameter is greater than the second diameter.

4. The tacking device of claim 1 wherein the head region curves between about 400 and 500 degrees total between the first end and the junction.

5. The tacking device of claim 1 wherein the curved portion comprises the first diameter and spans less than a full turn.

* * * * *